US00PP34028P2

(12) United States Plant Patent
Kobayashi

(10) Patent No.: US PP34,028 P2
(45) Date of Patent: Mar. 15, 2022

(54) **NEW GUINEA *IMPATIENS* PLANT NAMED 'DONGIROLCOCA'**

(50) Latin Name: *Inpatiens hawkeri*
Varietal Denomination: Dongirolcoca

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/230,876

(22) Filed: Apr. 14, 2021

(51) Int. Cl.
*A01H 5/02* (2018.01)
*A01H 6/16* (2018.01)

(52) U.S. Cl.
USPC ..... Plt./318.4
CPC ..... *A01H 6/16* (2018.05)

(58) Field of Classification Search
USPC ..... Plt./318.4
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Impatiens* plant named 'Dongirolcoca' characterized by its relatively compact, upright to outwardly spreading and uniformly mounding plant habit; moderately vigorous growth habit; freely branching habit; glossy and dark green-colored leaves; freely flowering habit; medium to large ruffled flowers that are light purplish pink in color; and good garden performance.

2 Drawing Sheets

Figure 1:
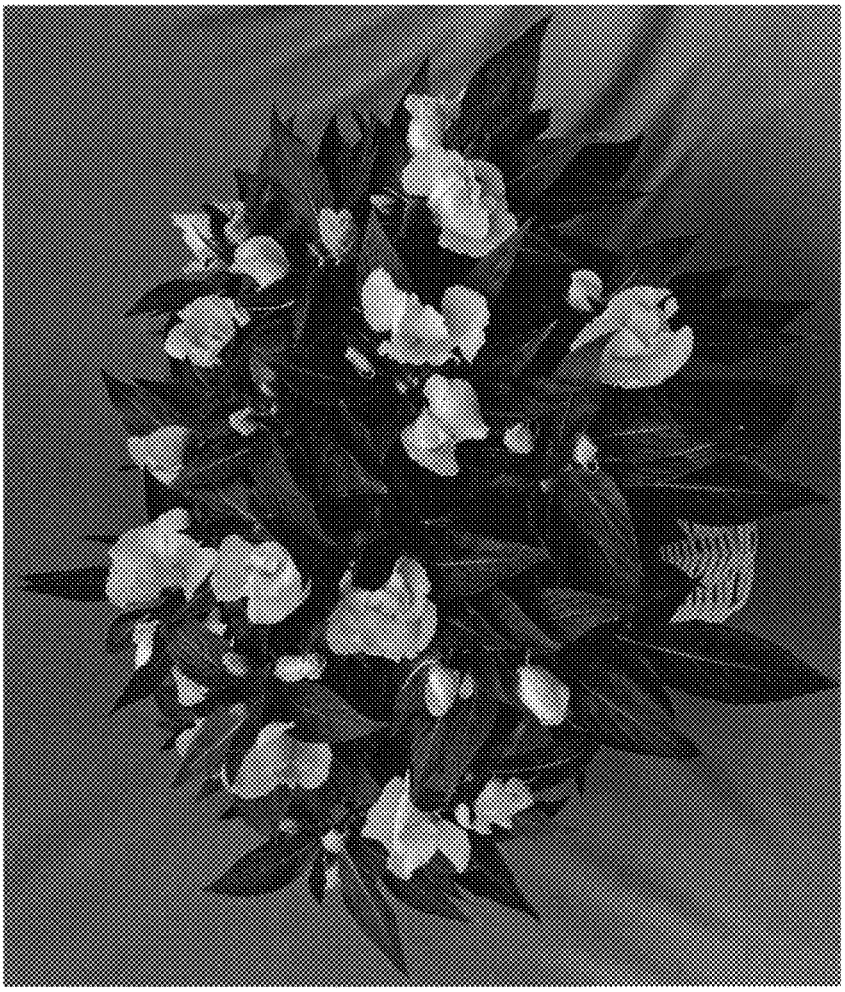

Botanical designation: *Impatiens hawkeri.*
Cultivar denomination: 'DONGIROLCOCA'.

CROSS-REFERENCED TO CLOSELY-RELATED APPLICATIONS

Title: New Guinea *Impatiens* Plant Named 'Dongirolsal'
Inventor: Ruth Kobayashi
Filed: Concurrently with the instant application, 17/230,915

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongirolcoca'.

The new *Impatiens* plant is a product of a planned breeding program conducted by the Inventor in Koka, Ethiopia and Encinitas, Calif. The objective of the breeding program is to create new freely branching and early and freely flowering New Guinea *Impatiens* plants with large attractive flowers and good garden performance.

The new *Impatiens* plant originated from a cross-pollination made by the Inventor in November, 2017 in Koka, Ethiopia of a proprietary selection of *Impatiens hawkeri* identified as code number NN15-571729-001, not patented, as the female, or seed, parent with *Impatiens hawkeri* 'Rococo Josephine 2016', not patented, as the male, or pollen, parent. The new *Impatiens* plant was discovered and selected by the Inventor as a single flowering plant from within the progeny of the stated cross-pollination in a controlled greenhouse environment in Encinitas, Calif. in April, 2018.

Asexual reproduction of the new *Impatiens* plant by terminal vegetative cuttings in a controlled greenhouse environment in Rheinberg, Germany since June, 2018 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongirolcoca'. These characteristics in combination distinguish 'Dongirolcoca' as a new and distinct *Impatiens* plant:

1. Relatively compact, upright to outwardly spreading and uniformly mounding plant habit.
2. Moderately vigorous growth habit.
3. Freely branching habit.

4. Glossy and dark green-colored leaves.
5 Freely flowering habit.
6. Medium to large ruffled flowers that are light purplish pink in color.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more compact than plants of the female parent selection.
2. Leaves of plants of the new *Impatiens* are lighter green in color than leaves of plants of the female parent selection.
3. Flowers of plants of the new *Impatiens* are more ruffled and undulating than flowers of plants of the female parent selection.
4. Flowers of plants of the new *Impatiens* are light purplish pink in color whereas flowers of plants of the female parent selection are lavender in color.

Plants of the new *Impatiens* can be compared to plants of the male parent, 'Rococo Josephine 2016'. Plants of the new *Impatiens* differ primarily from plants of 'Rococo Josephine 2016' in the following characteristics:

1. Flowers of plants of the new *Impatiens* are more ruffled and undulating than flowers of plants of 'Rococo Josephine 2016'.
2. Flowers of plants of the new *Impatiens* are light purplish pink in color whereas flowers of plants of 'Rococo Josephine 2016' are lavender pink in color.

Plants of the new *Impatiens* can be compared to plants of *Impatiens hawkeri* 'Dongirolsal', disclosed in U.S. Plant patent application Ser. No. 17/230,915 filed concurrently. In side-by-side comparisons, plants of the new *Impatiens* differ primarily from plants of 'Dongirolsal' in flower color as flowers of plants of the new *Impatiens* are light purplish pink in color whereas flowers of plants of 'Dongirolsal' are salmon pink in color.

Plants of the new *Impatiens* can be compared to plants of *Impatiens hawkeri* 'Kironanete', disclosed in U.S. Plant Pat. No. 26,753. In side-by-side comparisons, plants of the new *Impatiens* differ primarily from plants of 'Kironanete' in the following characteristics:

1. Plants of the new *Impatiens* have larger flowers than plants of 'Kironanete'.
2. Flowers of plants of the new *Impatiens* are more ruffled than flowers of plants of 'Kironanete'.
3. Flowers of plants of the new *Impatiens* are light purplish pink in color whereas flowers of plants of 'Kironanete' are dark cherry red in color.

Plants of the new *Impatiens* can also be compared to plants of *Impatiens hawkeri* 'Duemagpin', disclosed in U.S. Plant Pat. No. 25,035. In side-by-side comparisons, plants of the new *Impatiens* differ primarily from plants of 'Duemagpin' in the following characteristics:

1. Plants of the new *Impatiens* are more compact than and not as vigorous as plants of 'Duemagpin'.
2. Leaves of plants of the new *Impatiens* are lighter green in color than leaves of plants of 'Duemagpin'.
3. Flowers of plants of the new *Impatiens* are more ruffled than flowers of plants of 'Duemagpin'.
4. Flowers of plants of the new *Impatiens* are light purplish pink in color whereas flowers of plants of 'Duemagpin' are soft pink in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongirolcoca' grown in a container.

Figure 2:
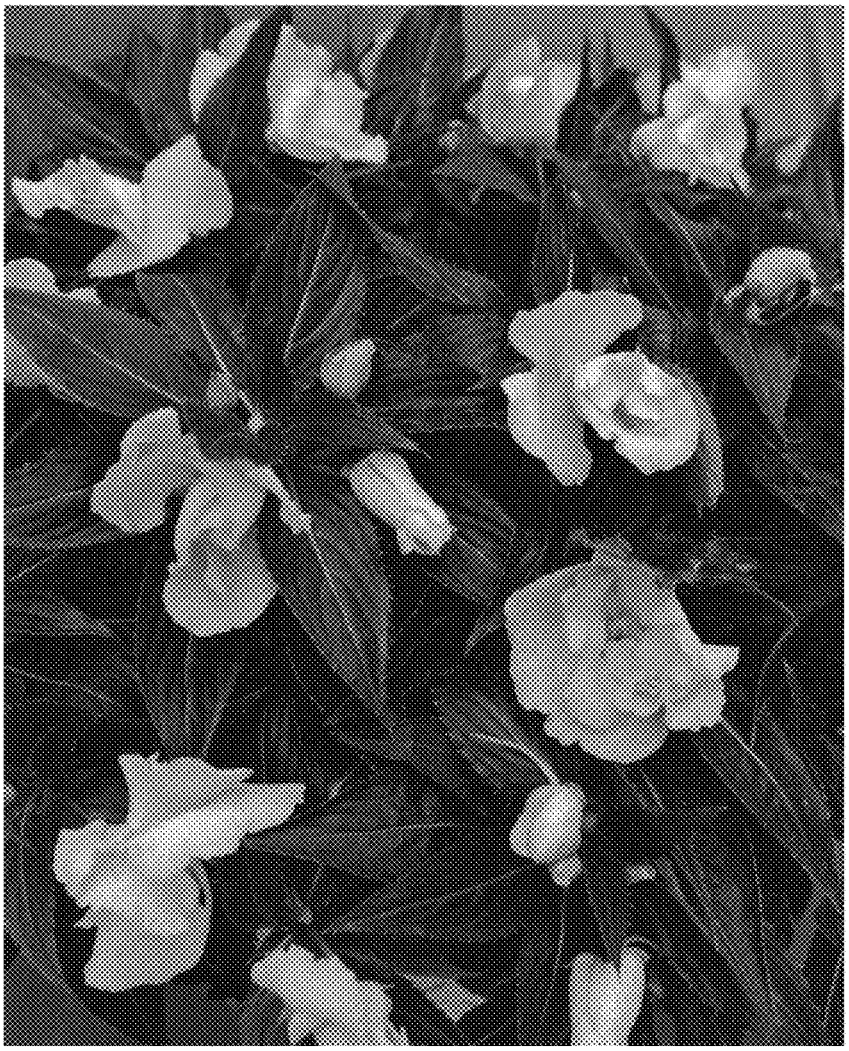

The photograph on the second sheet (FIG. 2) is a close-up view of a typical flowering plant of 'Dongirolcoca'.

DETAILED BOTANICAL DESCRIPTION

The aforementioned photographs and following observations, measurements and values describe plants grown during the summer in 16.5-cm containers in a polyethylene-covered greenhouse in Encinitas, Calif. and under cultural practices typical of commercial New Guinea *Impatiens* production. During the production of the plants, day temperatures averaged 25° C., night temperatures averaged 20° C. and light levels ranged from 4,000 to 4,500 lux. Plants were 14 weeks old when the photographs and description were taken. In the following description, color references are made to The Royal Horticultural Society Colour Chart, 2015 Edition, except where general terms of ordinary dictionary significance are used.

Botanical classification: *Impatiens hawkeri* 'Dongirolcoca'.

Parentage:

*Female, or seed, parent.*—Proprietary selection of *Impatiens hawkeri* identified as code number NN15-571729-001, not patented.

*Male, or pollen, parent.*—*Impatiens hawkeri* 'Rococo Josephine 2016', not patented.

Propagation:

*Type.*—By terminal vegetative cuttings.

*Time to initiate roots, summer and winter.*—About five to seven days at day temperatures about 27° C. and night temperatures about 20° C.

*Time to produce a rooted young plant, summer and winter.*—About three weeks at day temperatures about 27° C. and night temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Relatively compact, upright to outwardly spreading and uniformly mounding plant habit; broad inverted triangle in overall shape; freely branching habit; bushy and dense appearance; moderately vigorous growth habit and moderate growth rate; strong and sturdy plants.

*Plant height.*—About 23 cm.

*Plant diameter.*—About 44 cm.

Lateral branch description:

*Branching habit*.—Freely branching with about six to eight primary lateral branches each with multiple secondary branches.

*Length*.—About 19.5 cm.

*Diameter*.—About 1.4 cm.

*Internode length*.—About 5.2 cm to 6.3 cm.

*Strength*.—Strong, flexible.

*Aspect*.—Initially upright to about 45° from vertical to almost horizontal.

*Texture and luster*.—Smooth, glabrous; moderately glossy.

*Color, developing and developed*.—Close to 144A.

Leaf description:

*Arrangement*.—Typically in whorls or opposite; simple; leaves are durable.

*Length*.—About 11.5 cm.

*Width*.—About 4.75 cm.

*Shape*.—Narrowly to broadly ovate.

*Apex*.—Acuminate.

*Base*.—Attenuate.

*Margin*.—Serrate with ciliation.

*Texture and luster, upper surface*.—Smooth, glabrous; coriaceous; glossy.

*Texture and luster, lower surface*.—Smooth, glabrous; coriaceous; slightly glossy.

*Venation pattern*.—Pinnate; arcuate.

*Color*.—Developing leaves, upper surface: More green than 147A. Developing leaves, lower surface: Close to 147B. Fully expanded leaves, upper surface: Darker green than between 147A and N189A; midvein, close to 144A and lateral venation, darker green than between 147A and N189A. Fully expanded leaves, lower surface: Close to 147B; midvein, proximally, close to 147D and distally, close to 144A; and lateral venation, close to 146A.

*Petiole length*.—About 3.1 cm.

*Petiole diameter*.—About 3 mm.

*Petiole texture and luster, upper and lower surfaces*.—Smooth, glabrous; moderately glossy.

*Petiole color, upper surface*.—Close to 146B to 146C.

*Petiole color, lower surface*.—Close to 146C.

Flower description:

*Flower type and flowering habit*.—Medium to large ruffled single axillary flowers that are rounded to rounded rectangular in shape; freely flowering habit, typically about four to six flower buds and opened flowers per lateral branch; flowers are positioned above and beyond the foliar plane, flowers typically face mostly upright or outwardly to slightly nodding.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks from unrooted cuttings.

*Flower buds*.—Length: About 1 cm. Diameter: About 7.5 mm. Shape: Ovoid; flower buds resemble rose buds when opening. Texture and luster: Smooth, glabrous; glossy. Color: Close to 144A.

*Flower diameter*.—Medium to large, about 5.75 cm by 6 cm.

*Flower depth*.—About 2.2 cm.

*Petals*.—Quantity and arrangement: Five per flower in a single whorl with one banner petal, two lateral petals and two lower petals. Length, banner petal: About 3.4 cm. Length, lateral petals: About 3.1 cm. Length, lower petals: About 3.2 cm. Width, banner petal: About 4.7 cm. Width, lateral petals: About 4.4 cm. Width, lower petals: About 4.6 cm. Shape, all petals: Obcordate. Apex, all petals: Emarginate. Base, all petals: Truncate to attenuate. Margin, all petals: Entire; undulate and ruffled with occasional indentations. Texture and luster, all petals, upper and lower surfaces: Smooth, glabrous; slightly glossy; iridescent. Color, all petals: When opening, upper surface: Close to 62B; towards the base, close to 62D. When opening, lower surface: Close to 65C to 65D; towards the base, close to 54A. Fully opened, upper surface: Close to 62A; center, close to 62B to 62C; towards the base, close to 54A; with subsequent development, color becoming closer to 62C to 62D with center, close to 62D and towards the base, close to 54A. Fully opened, lower surface: Close to 65C to 65D; towards the margins, base and venation, close to 54A; midvein on banner, close to 144A; with subsequent development, color becoming closer to 65D and towards the base, margins and venation, close to 54A.

*Sepals*.—Quantity and arrangement: Three in a single whorl; two laterals are opposite and the third modified into an elongated spur. Lateral sepal length: About 1.1 cm. Lateral sepal width: About 7.5 mm. Lateral sepal shape: Broadly deltoid to ovate. Lateral sepal apex: Acuminate. Lateral sepal base: Truncate. Lateral sepal margin: Entire, not undulate. Lateral sepal texture and luster, upper and lower surfaces: Smooth, glabrous; moderately glossy. Lateral sepal color, upper surface: Close to 144C and 144D. Lateral sepal color, lower surface: Close to 144C. Spurred sepal length (not including spur): About 1.6 cm. Spurred sepal width (proximally): About 1 cm. Spurred sepal shape (proximally): Broadly ovate. Spurred sepal base: Truncate. Spurred sepal margin (proximally): Entire, not undulate. Spurred sepal texture and luster (proximally), upper and lower surfaces: Smooth, glabrous; moderately glossy. Spurred sepal color (proximally), upper surface: Close to 157A. Spurred sepal color (proximally), lower surface: Close to 157A and towards the apex, close to 144A. Spur length: About 3 cm. Spur diameter: At flower, about 2 mm; at apex, less than 1 mm. Spur shape: Acicular, curved. Spur texture and luster: Smooth, glabrous; glossy. Spur color: Close to 157A.

*Peduncles*.—Length: About 3.25 cm. Diameter: About 1.5 mm. Angle: About 45° to slightly arching. Strength: Strong; flexible. Texture and luster: Smooth, glabrous; glossy. Color: Close to 144B.

*Reproductive organs*.—Stamens: Quantity: Five fused at anthers; filaments free. Filament length: About 4 mm. Filament color: Close to 158A. Anther length: About 2.25 mm. Anther shape: Oblong. Anther color: Close to N155B. Pollen amount: Scarce. Pollen color: Close to 158A. Pistils: Quantity per flower: One. Pistil length: About 4.5 mm. Stigma shape: Crested. Stigma color: Close to 144A. Style length: About 4 mm. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongirolcoca' as illustrated and described.

* * * * *